United States Patent
Leung et al.

(10) Patent No.: US 7,799,021 B2
(45) Date of Patent: Sep. 21, 2010

(54) ELECTROSURGICAL TREATMENT IN CONJUNCTION WITH MONITORING

(75) Inventors: Mark Leung, Toronto (CA); Nir Lifshitz, Toronto (CA); Neil Godara, Mississauga (CA); Laura Conquergood, Mississauga (CA)

(73) Assignee: Kimberly-Clark Inc., Mississauga, Ontario (CA)

( * ) Notice: Subject to any disclaimer, the term of this patent is extended or adjusted under 35 U.S.C. 154(b) by 1193 days.

(21) Appl. No.: 11/198,099

(22) Filed: Aug. 4, 2005

(65) Prior Publication Data

US 2006/0030845 A1    Feb. 9, 2006

Related U.S. Application Data

(60) Provisional application No. 60/598,759, filed on Aug. 4, 2004.

(51) Int. Cl.
*A61B 18/18* (2006.01)
*A61N 1/00* (2006.01)

(52) U.S. Cl. .................. 606/41; 606/49; 607/2

(58) Field of Classification Search ............ 606/41–50; 607/122
See application file for complete search history.

(56) References Cited

U.S. PATENT DOCUMENTS

| | | | |
|---|---|---|---|
| 4,235,242 A | 11/1980 | Howson et al. | |
| 4,934,377 A | 6/1990 | Bova et al. | |
| 5,081,990 A | 1/1992 | Deletis | |
| 5,334,193 A * | 8/1994 | Nardella | 606/41 |
| 5,954,719 A * | 9/1999 | Chen et al. | 606/42 |
| 5,983,141 A * | 11/1999 | Sluijter et al. | 607/100 |
| 6,266,558 B1* | 7/2001 | Gozani et al. | 600/547 |
| RE40,279 E * | 4/2008 | Sluijter et al. | 607/100 |
| 2001/0014802 A1* | 8/2001 | Tu | 606/21 |
| 2003/0199862 A1* | 10/2003 | Simpson et al. | 606/34 |
| 2004/0006376 A1 | 1/2004 | Falci | |
| 2004/0122482 A1* | 6/2004 | Tung et al. | 607/48 |
| 2005/0004563 A1* | 1/2005 | Racz et al. | 606/34 |
| 2005/0182393 A1* | 8/2005 | Abboud et al. | 606/20 |
| 2005/0278007 A1* | 12/2005 | Godara | 607/105 |
| 2005/0283148 A1* | 12/2005 | Janssen et al. | 606/34 |
| 2006/0025702 A1* | 2/2006 | Sterrantino et al. | 600/554 |

OTHER PUBLICATIONS

Castello, PH et al. "Quantification of lumbar nerve root decompression using somatosensory-evoked potentials". Journal of Spinal Disorders (Medline abstract). 8(6):444-450. Dec. 1995.

(Continued)

*Primary Examiner*—Michael Peffley
*Assistant Examiner*—Ronald Hupczey, Jr.
(74) *Attorney, Agent, or Firm*—Dority & Manning, P.A.

(57) ABSTRACT

An electrosurgical apparatus comprising an energy source operable to concurrently provide a first signal and a second signal, said first and second signals having different frequencies; and a signal processor operable to receive a third signal from a patient's body, to process said third signal, and to produce an output based on a processing of said third signal; wherein said third signal is an evoked potential generated by said patient's body in response to a delivery of said second signal to said patient's body.

70 Claims, 5 Drawing Sheets

OTHER PUBLICATIONS

Padberg AM, Bridwell KH. "Spinal Cord Monitoring—Current State of the Art". Orthopedic Clinics of North America (Medline Abstract). 30(3):407-433. Jul. 1999.

Kalkman, CJ. "Spinal Cord Monitoring". European Society for Intravenous Anaesthesia, 7th annual meeting. Jun. 4, 2004.

Report of the Trigeminal Neuralgia Association, Second National Conference. Nov. 11, 1998.

NicoletOne—Modular Neurodiagnositc System. Brochure. Downloaded Aug. 2005.

* cited by examiner

Figure 6

ELECTROSURGICAL TREATMENT IN CONJUNCTION WITH MONITORING

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

With specific reference now to the drawings in detail, it is stressed that the particulars shown are by way of example and for purposes of illustrative discussion of the embodiments of the present invention only. In this regard, the description taken with the drawings making apparent to those skilled in the art how several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
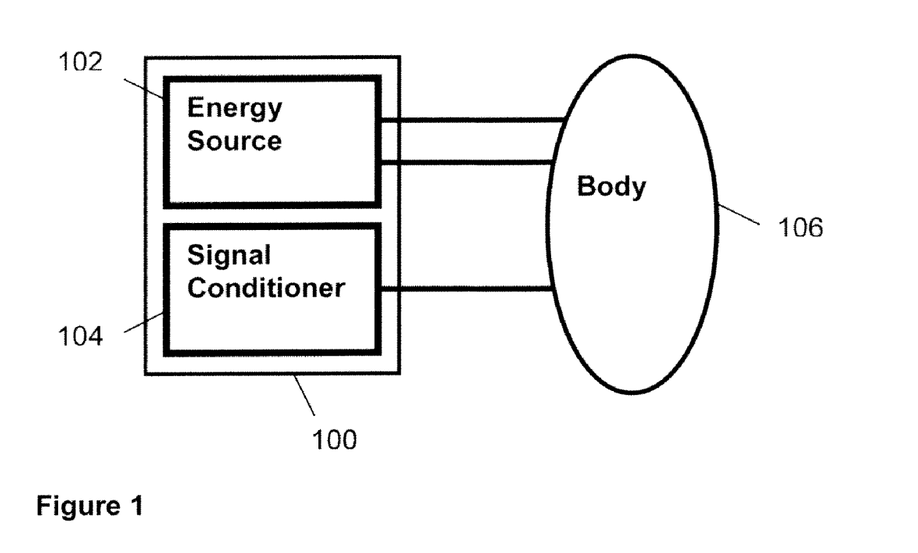
FIG. 1 is an illustration of one embodiment of an apparatus of the invention.

Referring now to the drawings, FIG. 1 represents one embodiment of an apparatus 100 of the invention, which comprises a means 102 for concurrently providing a first signal and a second signal, the first and second signals having different frequencies. Apparatus 100, in this embodiment, further comprises a means 104 for receiving a third signal from a patient's body 106, processing the third signal and producing an output based on the processing of the third signal.

As an example of the embodiment shown in FIG. 1, means 102 may comprise an energy source and means 104 may comprises a signal processor. In one embodiment, energy source 102 is operable to concurrently provide a first signal and a second signal having different frequencies by providing two separate and distinct signal generators. The signal generators may comprise function generators, waveform generators, oscillators, amplifiers and other electrical components necessary to produce electrical signals at a desired frequency. Each signal generator may reside on a separate printed circuit board or integrated circuit or they may be combined in a single integral unit. In an alternate embodiment, a single signal generator may be provided, the signal generator operable to produce a signal having two distinct frequency components. The distinct frequency components may then be separable by, for example, splitting the signal provided by the single signal generator into two signals and providing means for filtering the desired frequency component for each signal. For example, a first signal may be provided with a high pass filter allowing for the isolation of a high frequency component, while a second signal may be provided with a low pass filter allowing for the isolation of a low frequency component. Thus, energy source 102 may be operable to concurrently provide first and second signals having different frequencies in various ways. In further embodiments, more than two signals may be provided, and these signals may be produced as one or more separate and distinct signals.

In one embodiment, energy source 102 comprises a generator operable to provide at least one signal in the radio-frequency (RF) range, for example between about 260 kHz to about 1.5 MHz, and one signal at a lower frequency, for example between about 1 Hz and about 100 Hz. In a specific embodiment, a first RF signal may be delivered to a treatment site in a patient's body 106 in order to perform a treatment procedure at that site, and a second, lower frequency, signal may be delivered in order stimulate patient's body 106 to generate an evoked potential in response to the second signal.

Energy source 102 may comprise an incorporated means for displaying information. Said means for displaying information may include any apparatus operable to display any of a variety of information relevant to a procedure, including but not limited to: information regarding the operation of energy source 102 (for example, indications of instantaneous power, voltage, current, or frequency of one or more signals provided by energy source 102, or indications of how these parameters will change or have changed with time); information regarding the positioning of one or more devices within/on patient's body 106; information regarding characteristics of one or more sites within a body of a patient being treated, such as, but not limited to, temperature, impedance, or pressure; and information regarding informational messages such as errors or warnings related to a procedure. If no means for displaying information is incorporated into energy source 102, energy source 102 may comprise a means of transmitting a signal to an external display. Means for displaying information, either incorporated in or external to energy source 102 may comprise one or more of: screens or monitors (which may have text or graphical displays), LED or other illuminated indicators, gauges, dials, illuminated or liquid crystal digital displays (e.g. of alpha/numeric or other characters), or any other means of visual display.

In some embodiments, energy source 102 may further comprise a storage element, such as, but not limited to, a digital read-only memory (ROM) or random-access memory (RAM), an integrated or external hard drive, or a floppy, zip or CD/DVD drive. Energy source 102 may be operable to store data related to a treatment procedure using said storage element. One example of an RF generator that could be used with an embodiment of the invention is the Pain Management Generator (PMG) of Baylis Medical Company Inc. (Montreal, QC, Canada). Some embodiments of the invention may comprise an energy source 102 with one or more of the features described in co-pending U.S. patent application Ser. No. 10/122,413 to Shah et al, U.S. patent application Ser. No. 10/864,410 to Godara and U.S. patent application Ser. No. 10/893,274 to Godara, all of which are incorporated herein by reference.

As has been mentioned, one embodiment of the invention may comprise a signal processor 104 for receiving a signal from a patient's body 106, processing the signal and producing an output based on the processing of the signal. Signal processor 104 may comprise one or more filters for filtering the received signal, amplifiers for amplifying the received signal and one or more components for otherwise manipulating or analyzing the signal. Signal processor 104 may be operable to perform several functions, included but not limited to: comparing a signal to a predetermined or previously measured waveform or value, utilizing signal averaging or other signal analysis techniques to isolate a desired signal from a received signal, or processing, analyzing or modifying a signal in another way. After receiving and processing a signal from a patient's body 106, signal processor 104 may produce an output or it may alert a user in some fashion. For example, if signal processor 104 processes a received signal and detects a reduction in amplitude, as compared to a previously received signal, signal processor 104 may produce an audible alert, a visual alert, a vibration or another means that could be used to alert a user. In one embodiment, signal processor 104 may comprise one or more electrical connectors for receiving a signal, one or more electrical filters, such as high-pass or low-pass filters, one or more electrical amplifiers, and/or one or more circuits, algorithms, or physical devices operable to modify an electrical signal received from a patient's body 106. In some embodiments, signal processor 104 may be operable to receive a signal, wherein the signal received is an evoked potential generated by patient's body 106 in response to an applied signal. In one embodiment, signal processor 104 is thus able to receive and detect, measure, monitor, or sense one or more evoked potentials generated within a patient's body 106 in response to a signal provided by energy source 102. In some embodiments, said evoked potential may be at least one of somatosensory evoked potentials (SSEP), or motor evoked potentials (MEP). In other embodiments, signal processor 104 may be operable to receive a signal, wherein the signal received is indicative of a muscular response to motor nerve stimulation that may occur as a result of a treatment procedure. In such embodiments, the signal processor may be operable to detect an electromyographic response.

In some embodiments, signal processor 104 may comprise a means for displaying information incorporated into said signal processor 104. In other embodiments, signal processor 104 may comprise a means of transmitting a signal to an external display. Parameters displayed by a means for displaying information associated with signal processor 104 may include, but are not limited to: information regarding the operation of the signal processor (for example, indications of instantaneous power, voltage, current, or frequency of one or more signals received by signal processor 104, or indications of how these parameters will change or have changed with time); information regarding the positioning of one or more devices within/on patient's body 106; information regarding characteristics of one or more sites within a body of a patient, such as, but not limited to, temperature, impedance, or pressure; and information regarding informational messages such as errors or warnings related to a procedure. Means for displaying information associated with signal processor 104 may take a variety or forms, including but not limited to those described above with respect to energy source 102. In some embodiments, signal processor 104 and energy source 102 may share a means for displaying information. In such embodiments, the means for displaying information may be incorporated into a single housing, containing both signal processor 104 and energy source 102, or may be an external display.

In some embodiments of the present invention, apparatus 100 may further comprise means for inputting data (not shown). The means for inputting data may include, for example, a touch-screen interface, a keyboard, a mouse and/or various buttons, knobs and switches. Means for inputting data may allow a user to, for example, set operating parameters for energy source 102 and/or signal processor 104, input patient data or input treatment information. The treatment information may include, but is not limited to, the type of treatment procedure to be performed and the location of the treatment procedure to be performed.

Figure 2A:
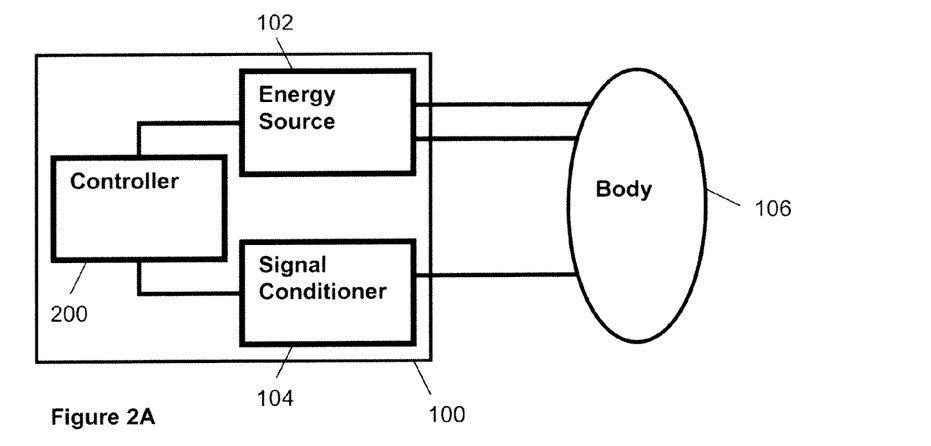
FIG. 2A is an illustration of an alternate embodiment of an apparatus of the invention.

In one embodiment, as shown in FIG. 2A, the apparatus of the present invention may further comprise a controller 200. In this embodiment, signal processor 104 may be coupled to, and communicate with, controller 200 via a cable, wire or other means for communication, which may be any means of communicating between two devices. For example, in some embodiments, the means for communicating between two devices may comprise: a physical cable (along with any associated connectors) such as an RS-232 cable, a USB cable, a firewire cable, or an ethernet cable; optical fibre; or one or more wireless communication mechanisms such as infrared, Bluetooth, satellite or another wireless communication protocol. Communication between signal processor 104 and controller 200 can be unidirectional or bi-directional.

In some embodiments, controller 200 may also be coupled to energy source 102 by any means of communication, as described above. In some embodiments comprising a controller 200, an output from signal processor 104, based on an evoked potential received by signal processor 104, is communicated to controller 200, which may be operable to alter an operation of energy source 102 in some way based on the output of signal processor 104. Controller 200 may alter an operation of energy source 102 by, for example: modulating the power output of energy source 102; disabling one or more operations of energy source 102; generating an informational messages such as an error or other alert to be displayed, stored in a storage element, or otherwise communicated to the user; or altering some other parameter controllable by energy source 102. In one embodiment, signal processor 104 is operable to receive an evoked potential from a patient's body 106, to monitor changes in this evoked potential over time and to analyse the received signal in order to establish a normalized, average measurement for the evoked potential. If the average voltage of the evoked potential changes, signal processor 104 may produce an output, which is communicated to controller 200. Controller 200 may then alter the operation of energy source 102 by for example, reducing the power, or may alter the operation of another component of the apparatus. For example, in one embodiment, controller 200 is operable to alter the operation of signal processor 104, for example, by altering filtering parameters, increasing or decreasing a level of amplification, or changing a predetermined or previously measured waveform or value to which a signal is compared.

Figure 2B:
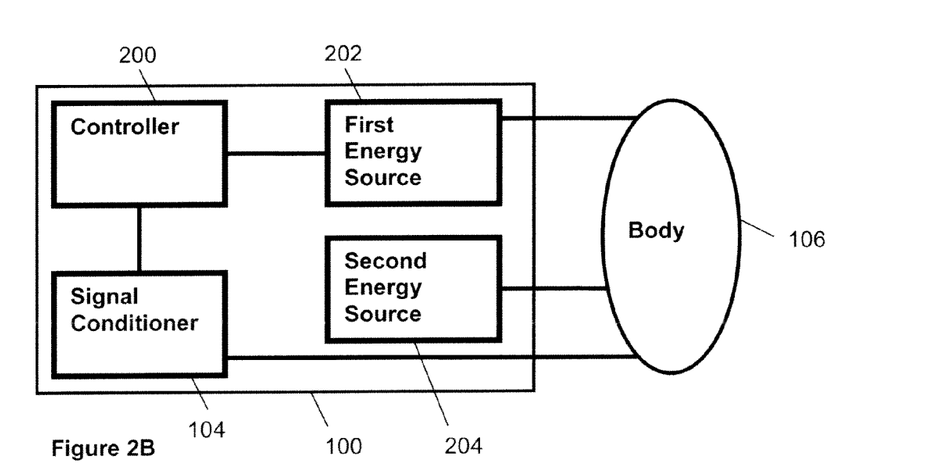
FIG. 2B is an illustration of a further embodiment of an apparatus of the present invention.

In another embodiment of the present invention, shown in FIG. 2B, the apparatus of the present invention may comprise: a means for providing a first signal having a first frequency; a means for providing a second signal having a second frequency; a means for receiving and processing a third signal from a patient's body 106 and producing an output based on the processing; and a means for controlling the first signal based on the output. The third signal may be an evoked potential generated by patient's body 106 in response to the application of the second signal to patient's body 106. As an example of this embodiment, the means for providing a first signal may comprise a first energy source 202, while the means for providing a second signal may comprise a second energy source 204. In addition, the means for receiving and processing the third signal and producing an output may comprise at least one signal processor 104. The means for controlling the first signal may comprise at least one controller 200 operable to alter an operation of the first energy source 202 based on the output of signal processor 104, for example as described above.

Figure 3:
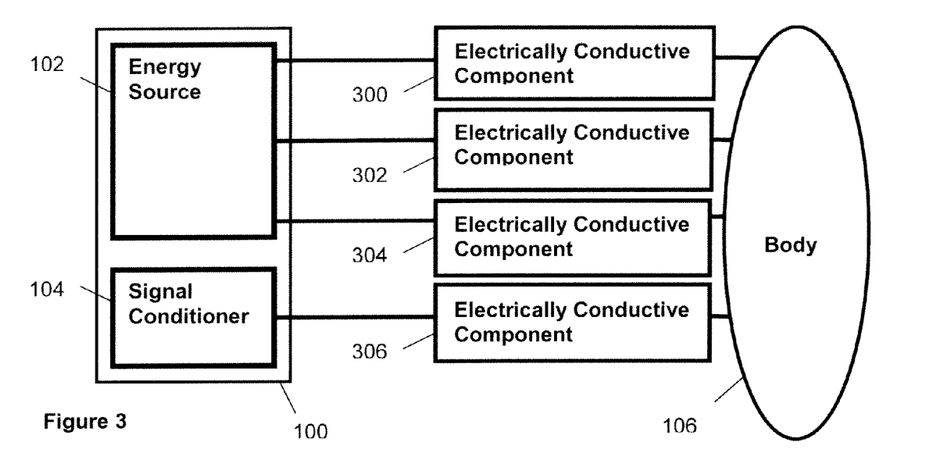
FIG. 3 is an illustration of an embodiment of a system of the invention.

FIG. 3 represents an embodiment of a system of the present invention comprising: an apparatus as shown in FIG. 1 and described in detail above; at least one electrically conductive component 300 operable to deliver a first signal to a patient's body 106; at least one electrically conductive component 302 operable to deliver a second signal to a patient's body 106; at least one electrically conductive component 304 operable to provide a return path for at least one of said first and second signals; and at least one electrically conductive component 306 operable to convey the evoked potential from patient's body 106 to energy source 102.

Electrically conductive components 300 and 302 may, in some embodiments, comprise electrosurgical probes, which may be operable to be electrically coupled to, depending on the specific embodiment, one or more of energy sources 102, 202 or 204, such that a signal provided by an energy source 102 can be delivered via components 300 and 302 to a patient's body 106. In such embodiments, these electrosurgical probes may have any of a variety of shapes, constructions and configurations. In one embodiment, component 300 may comprise an elongated, stainless steel probe, suitable for percutaneous insertion into a site in patient's body 106, and component 302 may comprise a surface electrode, capable of being affixed to a surface of a patient's body 106 and having a conductive region in contact with patient's body 106. In such an embodiment, the external surface of probe 300 may be overlain with an insulating material, such as polyethylene terephthalate (PETE), except for the distal tip of the probe, which may have an exposed conductive surface that serves as an electrode, and thus may be operable to deliver a signal to a region of tissue proximate to the distal tip. In other embodiments, a system of the present invention may comprise conductive components 300 and 302 with one or more features described in co-pending applications Ser. No. 11/105,527 to Leung et al; 60/593,839, 60/594,787, 60/595,426, 60/595,559 and 60/595,560 all to Godara et al; Ser. No. 11/125,247 to Hillier et al; Ser. No. 11/079,318 to Chandran et al; and 60/594,109 to Conquergood et al, all of which are incorporated herein by reference. In addition or alternatively, conductive components 300 or 302 may, in some embodiments, comprise an integrated device composed of two or more distinct parts, for example an integrated probe and cannula, or a combination of one or more individual devices, such as a cannula, a probe and a stylet that are all physically separable. In some embodiments, any of conductive components 300, 302, 304, and/or 306 may comprise surface or patch electrodes or needle electrodes. For example, conductive component 304 may, in some embodiments, comprise a dispersive electrode or grounding pad operable to be placed on a surface of a patient's body 106. Furthermore, any of conductive components 300, 302, 304, and/or 306 may, in certain embodiments, comprise a means of enhancing visualization, such as a marker to facilitate identification of said conductive component, or a region thereof, under X-ray fluoroscopy, such as a radiopaque marker.

In use of one embodiment of the present invention, an energy source (for example, one or more of energy sources 102, 202 and 204) is coupled to components 300 and 302 and provides a first signal having a frequency in the RF range and a power of, for example, 2-8 Watts, to conductive component 300; the delivery of the first signal into a region of tissue to a patient's body 106 may generate sufficient heat in the tissue to result in the formation of a lesion in the tissue adjacent said conductive component 300. In the context of this invention, a lesion refers to a destructive modification, such as, but not limited to, dehydration, denaturation, ablation, coagulation and/or lysis. In some other embodiments, delivery of energy in the form of a signal provided by an energy source may also result in a non-destructive effect, such as a modification of neural function; where the region of tissue comprises a neural structure, the transmission of energy, regardless of any destructive effect, may interfere with the transmission of a signal along a nerve associated with the neural structure, a process known as denervation.

In certain embodiments, the energy source may provide a first signal having a frequency in the RF range to one or more conductive components 300, and a second signal having a frequency in a physiological stimulation range (for example, 1 Hz-100 Hz) to one or more conductive components 302. Conductive component 306 may be electrically coupled to signal processor 104 for transmitting a signal from patient's body 106 to signal processor 104. Conductive component 300 may be positioned, for example, in the vicinity of a neural structure located with respect to the central nervous system of a patient's body 106, between the positions of conductive components 302 and 306. In such an embodiment, the delivery of the second signal via conductive component 302 may result in the generation of an evoked potential response receivable by conductive component 306 and transmitted, at least in part, by at least a portion of the neural structure in the vicinity of conductive component 300. Therefore, if the conductive properties of the neural structure were to be altered, for example due to the delivery of a signal from component 300, the transmission of the evoked potential may be affected. The evoked potential may be conveyed to signal processor 104 via component 306 and the effect on the evoked potential transmission may then be determined by signal processor 104.

For example, in one embodiment, a conductive component 300 may be positioned in the vicinity of the spinal cord, for example adjacent an intervertebral disc; a conductive component 302 may be positioned on the surface of an extremity of the patient; and a conductive component 306 may be positioned within or adjacent the patient's brain or spinal cord, cervical to the position of conductive component 300. Components 300 and 302 may be electrically coupled to an energy source 102 while component 306 may be electrically coupled to signal processor 104. In addition, component 304 may be electrically coupled to a current sink in order to provide a return path for any signals deposited into patient's body 106. Component 300 is operable to deliver a first signal to a region of tissue adjacent the intervertebral disc. Component 302 is operable to deliver a second signal to a patient's extremity to generate a sensory evoked potential that is then transmitted through the patient's central nervous system and is received by component 306 and conveyed to signal processor 104. If the delivery of the first signal to the tissue in the vicinity of conductive component 300 alters the function of neural tissue in the spinal cord responsible for conducting the sensory evoked potential from the patient's extremity, signal processor 104 may detect a change in the evoked potential. The general principle thought to be involved, for the purposes of explanation and simplification alone and without intending to limit any embodiment of the invention in any way, is that neurological signals travel from where they are first produced, along a specific pathway of the central nervous system, to the brain. If any neural structures along said specific pathway are perturbed, transmission of signals along said specific pathway may be affected. Thus, monitoring the transmission of signals from a production site to another site along a specific pathway of the central nervous system may be indicative of the viability of any neural structures along said specific pathway. Thus, monitoring the transmission of the evoked potential may help to: ensure that treatment of the neural structure has not affected portions of the central nervous system in an undesirable manner; or measure the efficacy of a treatment procedure with respect to the neural structure.

In some embodiments, the system of the present invention may additionally comprise at least one introducer device to aid in the positioning or insertion of at least one conductive component into patient's body 106. For example, if the region of tissue to be treated is a neural structure or tumor located within a bone of a patient's body 106, at least one introducer device, comprising, in one embodiment, a rigid, sharpened, hollow tube, may be used to access the bone and provide a path through which a conductive component may be introduced into the bone. Introducers may, in some embodiments, be sharpened, pointed, round, square, triangular, irregular in circumference, straight, bent, curved, elongated, truncated, rigid, flexible, tapered, straight, or have any other shape or structural characteristic.

Conductive component 304 may have various shapes and sizes, and may be adapted to be positioned at various locations on, in or adjacent patient's body 106. In some embodiments, conductive component 304 may be electrically coupled to a current sink. For example, in one embodiment, conductive component 304 comprises a grounding pad electrically coupled to an energy source 102 operable as a current sink, wherein component 304 has a surface area that is significantly larger than the surface area of any components used to deliver a signal to patient's body 106. Component 304 may be located on the surface of a patient's body, some distance away from any other conductive components.

In one embodiment, one or more conductive components 300 are operable to deliver a first signal in a monopolar configuration, the first signal being such that its application may cause one or more lesions to form around conductive components 300. The first signal may follow a return path provided by a conductive component 304; wherein the structure of conductive component 304 is such that no lesion is capable of forming in the vicinity of conductive component 304.

In another embodiment, conductive component 300 may comprise a bipolar apparatus, wherein a first signal is both delivered to patient's body 106 and returned from patient's body 106 through component 300. In other embodiments, any of conductive components 300, and 302 may comprise a multipolar electrical apparatus, for example a bipolar or triphasic apparatus, whereby signals conveyed by said conductive component may be transmitted between the various poles of the electrical apparatus.

Although energy source 102 is capable of concurrently providing two signals, for example, in some embodiments, a first signal having a frequency in the RF range, and a second low-frequency signal in the range of 1 Hz-100 Hz, said signals may also be provided independently. In one embodiment for example, a low-frequency second signal may be provided following the application of a high-frequency first signal, allowing a user to evaluate a surgical procedure as follows: prior to the commencement of a treatment procedure, conductive component 300 is placed within a region of tissue to be treated, the region of tissue to be treated comprising at least one neural structure. A conductive component 302 may be placed proximate a nerve (hereby referred to as a stimulated nerve) that transmits signals to the brain along a pathway comprising the neural structure. Conductive component 306 may then be placed at another point on or within a patient's body 106 further along said pathway, for example, on a patient's head. Prior to the delivery of the first signal, conductive component 302 may be operable to deliver the second signal to the stimulated nerve, causing the stimulated nerve to generate a pre-treatment evoked potential, which is received by conductive component 306 and conveyed to signal processor 104. The first signal may then be delivered via component 300. The delivery of the first signal by conductive component 300 may cause the denervation of said neural structure (thus interfering with the transmission of a sensory signal, such as a pain signal, in a nerve associated with said neural structure) and the denervation of said neural structure may interfere with the transmission of any signals that pass through said neural structure, included signals transmitted from the stimulated nerve. Following completion of any treatment of said neural structure, the second signal may again be delivered via conductive component 302, and a corresponding post-treatment evoked potential received by component 306 and conveyed to signal processor 104. The post-treatment evoked potential can then be compared to the pre-treatment evoked potential; if the denervation was successful, the post-treatment evoked potential may have a substantially lower amplitude than the pre-treatment evoked potential. It is to be understood that usage of an embodiment of the present invention in this manner, i.e. to measure efficacy of a treatment procedure, is also possible with the concurrent delivery of the first and second signals.

As has been mentioned with respect to apparatus 100, some embodiments of a system of the present invention may further comprise means for inputting data, as described above. Means for inputting data may be used by a user to input the location of one or more conductive components 300, 302, 304 and/or 306 at any time prior to, during, or after a treatment procedure. The location of the conductive components may be used, for example, to set operating parameters of one or more of the energy source and the signal processor.

Figure 4:
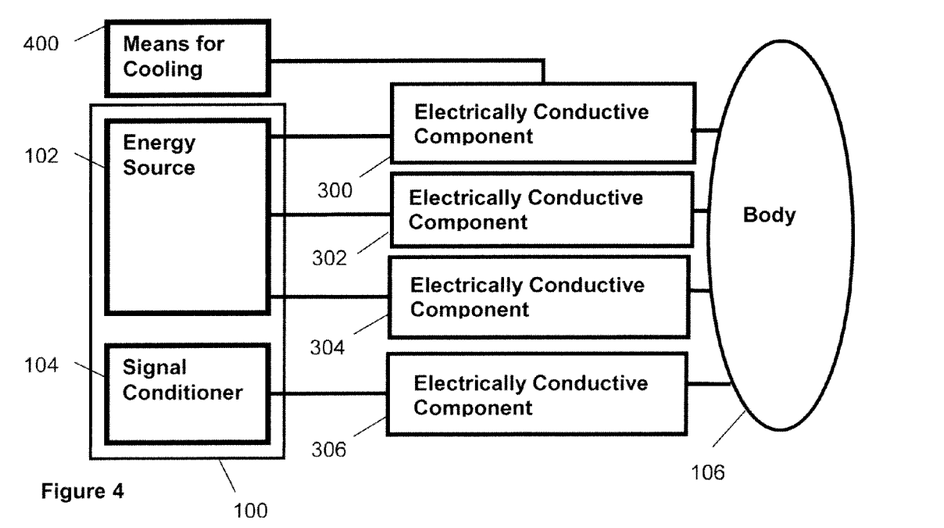
FIG. 4 is an illustration of an alternate embodiment of a system of the invention.

With reference now to FIG. 4, an alternate embodiment of a system additionally comprises at least one means 400 for cooling. Said means 400 for cooling may comprise any means of lowering a temperature of at least a portion of a region of tissue in a patient's body 106 adjacent one or more conductive components. In one embodiment, a means 400 for cooling may be a fluid circulation apparatus comprising one or more pumps (e.g. peristaltic pumps) operable to control the flow of a fluid at least one of to and from a conductive component to be cooled; in some embodiments said cooled conductive component may be furnished with one or more internal lumens to permit the circulation therethrough of a fluid. In another embodiment, a thermoelectric cooling device provides a means 400 for cooling a region of tissue, either by cooling said region of tissue directly, or by cooling a conductive component in the vicinity of said region of tissue, thereby potentially allowing for the conduction of heat away from said region of tissue through a conductive component. In some embodiments, a means 400 for cooling may be connected to and controllable by a controller 200. Communication between said means 400 for cooling and controller 200 may be unidirectional, allowing at least one operation of said means 400 for cooling to be controlled by controller 200, or to provide output to controller 200 to cause controller 200 to control an operation of another component of the system. For example, controller 200 may be operable to one or more of: modulate an output of said at least one means for cooling, disable one or more operations of said at least one means for cooling and otherwise alter a parameter controllable by said at least one means for cooling. Alternatively, communication between means 400 for cooling and controller 200 may be bi-directional, whereby controller 200 is both capable of controlling an operation of said means 400 for cooling, and capable of receiving an output from said means 400 for cooling.

Figure 5:
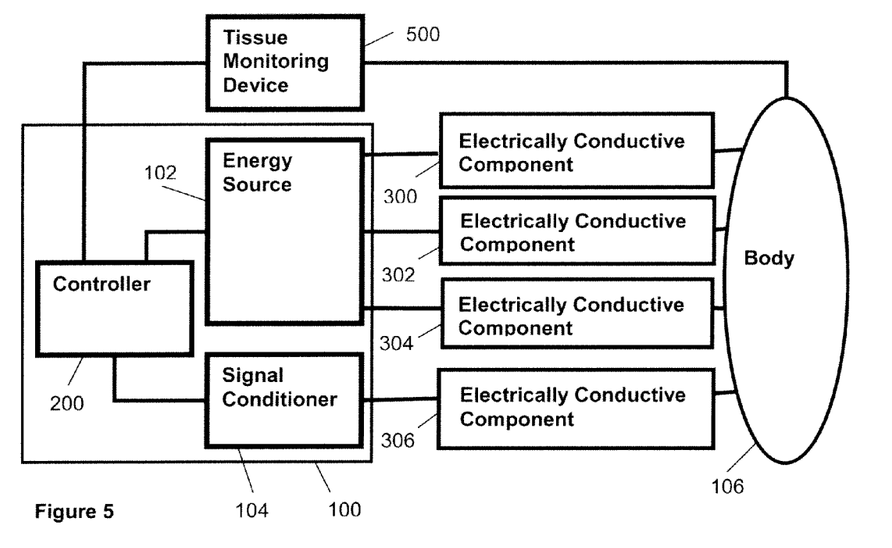
FIG. 5 is an illustration of a further embodiment of a system of the invention.

With reference now to FIG. 5, some embodiments of a system of the present invention may additionally comprise at least one tissue monitoring device 500. In such embodiments, the at least one tissue monitoring device 500 may comprise a means for monitoring one or more of temperature, impedance, pressure or any characteristic of a tissue of a patient's body 106. In one embodiment, at least one tissue monitoring device 500 may be integrated into one or more conductive components 300, 302, 304 or 306. For example, in one embodiment, a conductive component 300 operable to deliver a first signal provided by an energy source 102, may be furnished with a temperature sensor located in its distal tip and operable to measure temperature proximate to said distal tip of conductive component 300. In other embodiments, tissue monitoring devices 500 may be distinct devices and may not be integrated into any of conductive components 300, 302, 304, and/or 306.

When at least one tissue monitoring device 500 is a means for monitoring temperature, at least one tissue monitoring device 500 may comprise a temperature sensor, for example one or more of a thermocouple, a thermistor, a thermometer or some other means for measuring temperature. In embodiments where the delivery of a first signal having a frequency in the RF range is capable of causing the formation of a lesion in a region of tissue in a patient's body 106, monitoring the temperature may provide an indication as to the extent of lesion formation. Monitoring the impedance of a tissue being treated may also, in some embodiments, provide an indication as to the treatment's progression due to the fact that tissue impedance may vary as a consequence of the treatment being performed.

In some embodiments, at least one tissue monitoring device 500 is coupled to controller 200, and controller 200 is operable to alter the operation of a component of the system of the present invention based on an output from said at least one tissue monitoring device 500. For example, in one embodiment, the at least one monitoring device is operable to monitor temperature. In such an embodiment, controller 200 may be operable to receive a signal from said tissue monitoring device 500 indicative of the temperature of a tissue proximate to tissue monitoring device 500 and may further be operable to analyze such a signal, for example by comparing it to a preset temperature threshold. Based on the analysis, controller 200 may be operable to, for example, reduce the power of at least one signal provided by energy source 102.

A system or apparatus of the present invention has many applications and may be beneficial in any procedure incorporating an electrical generator for treatment of a region of tissue located in a patient's body 106, for example in the back. Examples of such procedures include but are not limited to: treatments of a patient's intervertebral disc, such as thermal annuloplasty, intradiscal therapy or transdiscal therapy; ablation of tumors proximate to a patient's spine; intraosseous ablation; facet joint ablation; and sacroiliac joint ablation.

Figure 6:
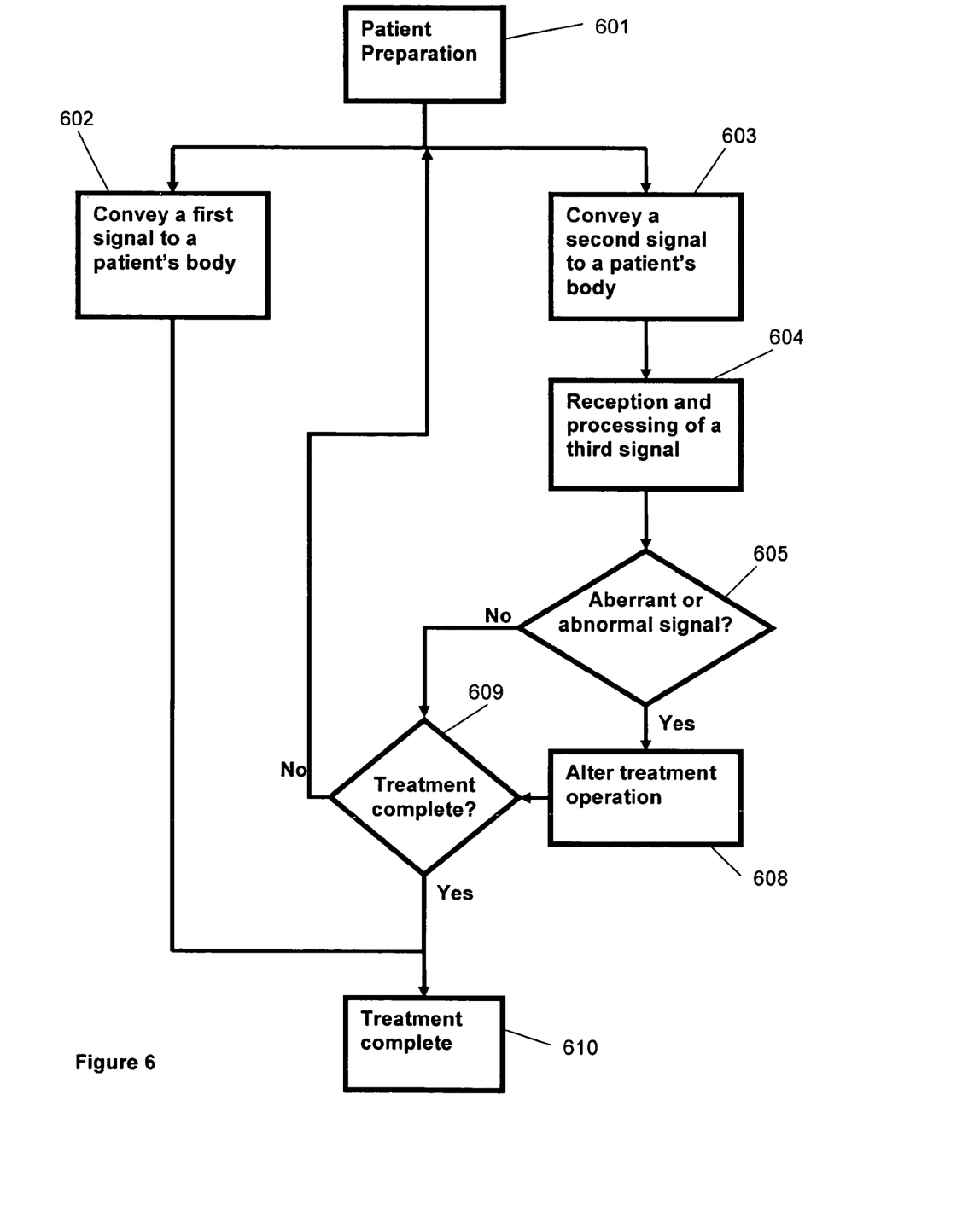
FIG. 6 is a flow-chart illustrating one embodiment of a method aspect of the present invention.

As an overview of a method aspect of the present invention, FIG. 6 illustrates a general method for one embodiment of a surgical procedure that may incorporate a system aspect of the present invention. Step 601 refers to any action associated with preparing the patient for the treatment procedure. Step 601 may comprise positioning at least one conductive component on or in a patient's body. The positioning of one or more conductive components may be facilitated by the use of imaging techniques, including, for example, X-ray fluoroscopy, and one or more of the conductive components may be marked in such a way that different regions of said conductive components are distinguishable from each other under fluoroscopy. Step 601 may further comprise other actions, including but not limited to setting up any equipment to be used in the treatment procedure.

In one embodiment, positioning at least one conductive component comprises: positioning a conductive component operable to deliver a first signal from an energy source adjacent a treatment site in a patient's body, for example, adjacent a neural structure such as a facet nerve of the spine of a patient; positioning a second conductive component operable to deliver a second signal from an energy source on or within a patient's body adjacent a location containing one or more nerves whose stimulation by the delivery of said second signal may generate an evoked potential that is conducted at least in part via said neural structure (e.g. said facet nerve); positioning a third conductive component operable to provide a return path, such as a grounding pad, on the surface of a patient's body, for example at a location relatively spaced apart from either of said first and second conductive components; and positioning a fourth conductive component within or adjacent a structure of a central nervous system (CNS) of the patient (for example, in a brain or spinal cord of said patient) such that said fourth conductive component is positioned closer to the brain of said patient (along the CNS pathway) than said first conductive component. Thus, an evoked potential generated by the delivery of said second signal would have to travel through said neural structure prior to being received by said fourth conductive component. In one embodiment comprising the positioning steps just having been described, the system may be configured to allow the generation and reception of a somatosensory evoked potential (SSEP).

In another embodiment, the step of positioning a conductive component comprises: positioning a conductive component operable to deliver a first signal from an energy source adjacent a treatment site in a patient's body, for example, adjacent a neural structure such as a facet nerve of the spine of a patient; positioning a second conductive component operable to deliver a second signal from an energy source within a portion of a brain of the patient, or at a location on the surface of a scalp of the patient, whereby the delivery of said second signal by said conductive component may generate an evoked potential that is conducted at least in part via said neural structure (e.g. said facet nerve); positioning a third conductive component operable to provide a return path, such as a grounding pad, on the surface of a patient's body for example at a location relatively spaced apart from either of said first and second conductive components; and positioning a fourth conductive component within or adjacent a tissue of a patient comprising, at least in part, one or more structures (for example, one or more muscles) innervated by nerves capable of being stimulated by an evoked potential produced by the delivery of said second signal to said portion of said brain or said scalp, whereby said first component is located between said second and forth components, with respect to the neural pathways of the central nervous system. Thus, an evoked potential generated by the delivery of said second signal would have to travel through said neural structure to component 306. In one embodiment comprising the positioning steps just having been described, the system may be configured to allow the generation and reception of a motor evoked potential (MEP).

In some embodiments, the first signal provided by an energy source to a conductive component has a frequency in the RF range and is capable of generating sufficient heat in a region of tissue in the vicinity of said first conductive component to result in the formation of a lesion in that region of tissue (for example, where the first signal has a power of approximately 2-8 W). Furthermore, the second signal provided by an energy source to a second conductive component may have, in some embodiments, a frequency in the physiological stimulation range and may be capable of generating an evoked potential when the second signal is delivered to a patient's body.

In some embodiments, the step of positioning a conductive component may comprise positioning a second conductive component at a location as far as possible from a first conductive component, while still being positioned in such a way that an evoked potential generated in response to the delivery of the second signal by said second conductive component will be conducted, at least in part, through a neural structure in the vicinity of said first conductive component. Similarly, in such embodiments, the step of positioning a third conductive component may involve the positioning of said third conductive component relatively close to said first conductive component, with respect to the position of said second conductive component. Furthermore, a fourth conductive component may be positioned as far as possible from said first conductive component, while still being operable to receive the evoked potential.

Step 601 may further comprise a step of inputting data using means for inputting data as described above. As has already been mentioned, the step of inputting data may include inputting the location of one or more conductive components 300, 302, 304 and/or 306. Alternatively or in addition, the step of inputting data may include inputting patient information and/or treatment information.

Step 602 comprises conveying a first signal, having a first frequency, to a patient's body, for example, by providing said first signal to at least one first conductive component operable to deliver said first signal to said patient's body. Step 603 comprises conveying a second signal, having a second frequency, to the patient's body, for example by providing said second signal to at least one second conductive component operable to deliver said second signal to said patient's body. In one embodiment, steps 602 and 603 occur substantially in parallel, being initiated and terminated approximately coincidentally. In other embodiments, one of steps 602 and 603 may be initiated prior to the other of steps 602 and 603, or one of steps 602 and 603 may be terminated prior to the termination of the other of steps 602 and 603. In yet other embodiments, the delivery of a signal during one or both of steps 602 and 603 may not be continuous so that at times only one of steps 602 and 603 are proceeding, and at times, both may be proceeding. Any and all such embodiments, whereby the delivery of the first signal and the delivery of the second signal occur at least partially coincidentally, are referred to throughout this specification, including the appended claims, using the term concurrently. Thus, the term 'simultaneously' is used to refer to two events occurring at substantially the same time while the terms 'concurrently' or 'partly concurrently' are used to refer to two events occurring at least partially at the same time.

In some embodiments, the step 602 of conveying a first signal to a patient's body comprises the delivery of a signal provided by an energy source via a first conductive component, the signal having a frequency in the RF range and being capable of generating sufficient heat in a region of tissue in the vicinity of said first conductive component to result in the formation of a lesion in said region of tissue. For example, as described above in relation to the operation of said first conductive component, the first signal may have a frequency in the range of about 260 kHz to about 5 MHz and a power of about 2 W to about 8 W. In some embodiments, the step 603 of conveying a second signal to a patient's body comprises the delivery of a signal provided by an energy source via a second conductive component, the signal having a frequency in the physiological stimulation range and being capable of causing the generation of an evoked potential. For example, the second signal may have a frequency in the range of about 1 Hz to about 100 Hz and a voltage of about 1 mW to about 400 W. In one specific embodiment, the second signal may be delivered to a tissue of a patient's body 106 containing one or more sensory nerves via said second conductive component having the form of a needle electrode inserted into said tissue or a surface electrode applied to a surface of a patient's body in the vicinity of said tissue. The delivery of the second signal may generate an evoked potential originating from one or more sensory nerves; the evoked potential may be receivable by a second conductive component inserted into or on a surface of a body in the vicinity of the brain or spinal cord of the patient. The evoked potential of this embodiment may be a somatosensory evoked potential. In another embodiment, the second signal may be delivered to region of a brain of a patient (for example, via a second conductive component placed on the surface of a scalp of said patient), and this delivery may generate an evoked potential in muscles innervated by motor nerves stimulated by the stimulation of said region of the brain. The evoked potential of this embodiment may be a motor evoked potential (MEP). In such an embodiment, a fourth conductive component may be placed in the vicinity of the innervated muscles in order to receive the evoked potential.

Step 604 comprises reception of a third signal by a signal processor, and, in some embodiments, processing of the third signal by said signal processor. In one embodiment, the third signal is an evoked potential generated in response to the delivery of the second signal by a second conductive component. If an aberrant or abnormal signal is received by said signal processor (Step 605, Yes branch), said signal processor may produce an output in the form of a communication to a controller, or a means for alerting the user to the aberrant or abnormal signal (Step 606); this alert can take one of several forms, as has been discussed earlier. At this point (Step 608), at least one aspect of the treatment procedure may be altered depending on the type and scope of the aberrant or abnormal signal that was received. In one embodiment, the treatment procedure may be altered automatically by said controller (i.e. with no user intervention), whereas in another embodiment, the treatment procedure may be altered by a user, for example in response to an alert produced by said signal processor. In either case, altering the treatment procedure may comprise: aborting the procedure altogether, stopping and restarting an energy source, modulating the output of an energy source (e.g. the power of one or more signals provided by the energy source), modulating an operation of a means for cooling, or modulating an operation of any other device used in the treatment procedure. The final step of the treatment procedure (Step 610) comprises termination of the procedure, which may occur upon the successful completion of the treatment procedure (Step 609, Yes branch) or upon premature abortion of the treatment procedure for any of a number of reasons.

Depending on the specific procedure being performed and the equipment available, a method of the present invention may further comprise one or more additional steps. Furthermore, FIG. 6 and the detailed description thereof are intended to be exemplary only. Any and all other methods involving the use of a system aspect of the present invention are intended to be included in the scope of the present invention.

In addition, although the invention has been described as useful for monitoring conduction along a patient's spine, it is clear to those well versed in the art that a system and method of the present invention are similarly applicable to any neural pathway of a body and are not limited specifically to be used only for monitoring the spinal cord itself.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, these embodiments are intended to be exemplary only and it is evident that many alternatives, modifications and variations will be apparent to those skilled in the art. Accordingly, the invention is intended to embrace all such alternatives, modifications and variations that fall within the spirit and broad scope of the appended claims.

We claim:

1. An electrosurgical apparatus comprising:
   at least one energy source operable to at least partly concurrently provide a first signal and a second signal, said first and second signals having different frequencies, said at least one energy source being operable to deliver said first signal to a first electrically conductive component for treating a region of tissue within a patient's body, said region of tissue comprising a neural structure, said at least one energy source being operable to deliver said second signal to a second electrically conductive component for stimulating the production of a third signal by a nerve within said patient's body for transmission along a neural pathway of said patient's body, said third signal being transmitted along said neural pathway at least partly concurrently with the provision of said first signal to said patient's body; and
   at least one signal processor operable to receive said third signal, to process said third signal, and to produce an output based on a processing of said third signal, said output being indicative of an effect of said first signal on said neural pathway along which said third signal is being transmitted.

2. The apparatus of claim 1, wherein said first signal has a frequency from about 260 kHz to about 1.5 MHz.

3. The apparatus of claim 1, wherein said second signal has a frequency from about 1 Hz to about 100 Hz.

4. The apparatus of claim 1, wherein said first signal has a frequency from about 260 kHz to about 1.5 MHz and wherein said second signal has a frequency from about 1 Hz to about 100 Hz.

5. The apparatus of claim 1, further comprising a controller.

6. The apparatus of claim 5, wherein said controller is operable to alter the operation of said at least one energy source.

7. The apparatus of claim 6, wherein said controller is operable to perform at least one operation selected from the group consisting of modulating a power output of said at least one energy source, disabling one or more operations of said at least one energy source and otherwise altering a parameter directly affected by an operation of said at least one energy source.

8. The apparatus of claim 5, wherein said controller is operable to control said at least one signal processor.

9. The apparatus of claim 8, wherein said at least one signal processor is operable to process said third signal by one or more of filtering said third signal using at least one filtering parameter, amplifying said third signal and comparing said third signal to a predetermined or previously measured waveform or value, and wherein said controller is operable to perform at least one operation selected from the group consisting of altering one or more of said at least one filtering parameters, increasing or decreasing a level of the amplification of said third signal, and changing said predetermined or previously measured waveform or value to which said third signal is compared.

10. The apparatus of claim 5, wherein said controller is operable to output an informational message.

11. The apparatus of claim 5, wherein said controller is operable to control said first signal based on said output.

12. The apparatus of claim 5, wherein said controller is operable to automatically alter an operation of said at least one energy source based on said output.

13. The apparatus of claim 1, wherein said neural pathway comprises said neural structure.

14. The apparatus of claim 1, wherein said neural pathway does not comprise said neural structure.

15. The apparatus of claim 1, wherein said at least one energy source comprises two separate and distinct signal generators.

16. The apparatus of claim 15, wherein each said signal generator may comprise at least one of a function generator, a waveform generator, an oscillator or an amplifier.

17. The apparatus of claim 15, wherein said two separate and distinct signal generators reside on a single circuit board or integrated circuit.

18. The apparatus of claim 1, wherein said at least one energy source comprises a single signal generator operable to produce a signal having two distinct frequency components.

19. The apparatus of claim 18, further comprising means for splitting said signal having two distinct frequency components into two signals and means for filtering said two signals.

20. An electrosurgical system comprising:
   an electrosurgical apparatus comprising at least one energy source operable to at least partly concurrently provide a first signal and a second signal, said first and second signals having different frequencies, and at least one signal processor operable to receive a third signal from a patient's body, to process said third signal, and to produce an output based on the processing of said third signal, wherein said third signal is an evoked potential generated by said patient's body in response to the application of said second signal to said patient's body;
   at least one electrically conductive component operable to deliver said first signal to a patient's body;
   at least one electrically conductive component operable to deliver said second signal to a patient's body;
   at least one electrically conductive component operable to convey said evoked potential from said patient's body to said signal processor; and
   at least one electrically conductive component operable to provide a return path for at least one of said first signal and said second signal.

21. The system of claim 20, wherein said first signal has a frequency from about 260 kHz to about 1.5 MHz.

22. The system of claim 20, wherein said second signal has a frequency from about 1 Hz to about 100 Hz.

23. The system of claim 20, wherein said first signal has a frequency from about 260 kHz to about 1.5 MHz and wherein said second signal has a frequency from about 1 Hz to about 100 Hz.

24. The system of claim 20, further comprising at feast one means for cooling coupled to one or more of said electrically conductive components.

25. The system of claim 24, wherein said means for cooling comprises at least one fluid circulation apparatus.

26. The system of claim 24, further comprising a controller coupled to said means for cooling.

27. The system of claim 26, wherein said controller is operable to alter an operation of said means for cooling.

28. The system of claim 27, wherein said controller is operable to perform at least one operation selected from the group consisting of modulating an output of said at least one means for cooling, disabling one or more operations of said at least one means for cooling and otherwise altering a parameter controllable by said at least one means for cooling.

29. The system of claim 20, further comprising at least one tissue monitoring device.

30. The system of claim 29, wherein said tissue monitoring device comprises a temperature sensor.

31. The system of claim 30, wherein said temperature sensor is selected from the group consisting of a thermocouple, a thermistor and a thermometer.

32. The system of claim 29, wherein said tissue monitoring device comprises an impedance monitor.

33. The system of claim 29, further comprising a controller.

34. The system of claim 33, wherein said controller is operable to alter an operation of a component of said system based on an output from said at least one tissue monitoring device.

35. The system of claim 20, wherein the at least one component operable to deliver said first signal comprises a probe.

36. The system of claim 20, wherein the at least one component operable to deliver said first signal comprises a bipolar apparatus.

37. The system of claim 20, wherein the at least one component operable to deliver said second signal is selected from the group consisting of a needle electrode and a surface electrode.

38. The system of claim 20, wherein the at least one component operable to convey said evoked potential is selected from the group consisting of a needle electrode and a surface electrode.

39. The system of claim 20, wherein the at least one component operable to provide a return path comprises a grounding pad.

40. The system of claim 20, wherein said at least one electrically conductive component operable to deliver said first signal to a patient's body is located between said at least one electrically conductive component operable to deliver said second signal to a patient's body and said at least one electrically conductive component operable to convey said evoked potential from said patient's body to said signal processor.

41. A method of electrosurgery comprising the steps of:
conveying a first signal having a first frequency to a patient's body through a first electrically conductive component;
conveying a second signal having a second frequency to a patient's body through a second electrically conductive component;
receiving an evoked potential generated by said patient's body through a third electrically conductive component, wherein said evoked potential is generated in response to a delivery of said second signal to said patient's body; and
processing said evoked potential and providing an output based on said processing of said evoked potential, said output being indicative of an effect of said first signal on said evoked potential;
wherein the steps of conveying a first signal and conveying a second signal occur at least partly concurrently.

42. The method of claim 41, wherein the step of processing said evoked potential comprises performing at least one operation selected from the group consisting of amplifying said evoked potential, filtering said evoked potential, averaging said evoked potential and comparing said evoked potential to a predetermined or previously measured waveform or value.

43. The method of claim 41, wherein said first signal has a frequency from about 260 kHz to about 1.5 MHz.

44. The method of claim 43, wherein said first signal is conveyed to perform at least one treatment procedure selected from the group consisting of lesioning, ablation and denervation.

45. The method of claim 41, wherein said second signal has a frequency from about 1 Hz to about 100 Hz.

46. The method of claim 45, wherein said second signal is conveyed to stimulate a sensory nerve.

47. The method of claim 46, wherein said evoked potential is a somatosensory evoked potential.

48. The method of claim 45, wherein said second signal is conveyed to stimulate a motor nerve.

49. The method of claim 48, wherein said evoked potential is a motor evoked potential.

50. The method of claim 41, wherein said first signal has a frequency from about 260 kHz to about 1.5 MHz and wherein said second signal has a frequency from about 1 Hz to about 100 Hz.

51. The method of claim 41, further comprising a step of altering said first signal based on said output.

52. The method of claim 41, further comprising a step of altering the processing of said evoked potential.

53. The method of claim 41, further comprising a step of outputting an informational message.

54. The method of claim 41, wherein said method further comprises a step of providing cooling.

55. The method of claim 54, further comprising a step of altering the cooling.

56. The method of claim 41, further comprising a step of monitoring at least one characteristic of a tissue of said patients body.

57. The method of claim 56, further comprising a step of altering said first signal based on the monitoring of the at least one tissue characteristic.

58. The method of claim 56, further comprising the steps of providing cooling and altering the cooling based on the monitoring of the at least one tissue characteristic.

59. The method of claim 41 wherein said first electrically conductive component is placed in the vicinity of a neural structure of a patient's body, said neural structure located, with respect to a neural pathway along which said evoked potential is being transmitted, between said second electrically conductive component and said third electrically conductive component.

60. The method of claim 41, wherein said first electrically conductive component is placed in the vicinity of a neural structure and said second electrically conductive component is placed proximate a nerve along a neural pathway comprising said neural structure.

61. The method of claim 41, wherein said first electrically conductive component is placed in the vicinity of a neural structure and said second electrically conductive component is placed proximate a nerve along a neural pathway of the central nervous system, wherein said neural pathway does not comprise said neural structure.

62. The method of claim 41, wherein said first signal is conveyed for treatment of a region of tissue within said patient's body.

63. The method of claim 41, wherein said first electrically conductive component and said second electrically conductive component are positioned at spaced apart sites within said patient's body.

64. The method of claim 63, wherein said first electrically conductive component is placed in the vicinity of a neural structure of said patient's body, said neural structure being located, with respect to a neural pathway along which said evoked potential is being transmitted, between said second electrically conductive component and said third electrically conductive component.

65. The method of claim 64, wherein said neural structure comprises a facet nerve, and wherein said second electrically conductive component is positioned adjacent a location containing one or more neural structures whose stimulation by said second signal may generate said evoked potential to be conducted by said facet nerve, and wherein said third electrically conductive component is positioned within or adjacent a structure of the central nervous system such that said third electrically conductive component is closer to a brain of said patient relative to said second electrically conductive component.

66. The method of claim 64, wherein said neural structure comprises a facet nerve, and wherein said second electrically conductive component is positioned within a brain or on a location on the surface of a scalp of the patient whereby delivery of said second signal by said second electrically conductive component may generate said evoked potential to be conducted at least in part by said facet nerve, and wherein said third electrically conductive component is positioned within or adjacent one or more muscles innervated by nerves capable of being stimulated by said evoked potential.

67. An electrosurgical apparatus comprising:
a first energy source operable to provide a first signal having a first frequency;
a first electrically conductive component for delivering said first signal from said first energy source to a patient's body;
a second energy source operable to provide a second signal having a second frequency;
a second electrically conductive component for delivering said second signal from said second energy source to said patient's body;
a third electrically conductive component for receiving a third signal generated by said patient's body in response to said second signal and for conveying said third signal to a signal processor, said signal processor operable to receive said third signal, to process said third signal, and to produce an output based on the processing of said third signal; and
a controller operable to control said first signal based on said output;
wherein said third signal is an evoked potential generated by said patient's body in response to the delivery of said second signal to said patient's body.

68. The apparatus of claim 67, further comprising a display.

69. An electrosurgical apparatus comprising:
means for at least partly concurrently providing at least a first signal and a second signal, said first and second signals having different frequencies;
means for delivering said first signal to a patient's body;
means for delivering said second signal to a patient's body;
means for receiving a third signal from a patient's body;
means for processing said third signal, for producing an output based on the processing of said third signal;
means for conveying said third signal from said signal receiving means to said means for processing said third signal; and
means for controlling said first signal based on said output;
wherein said third signal is an evoked potential generated by said patient's body in response to the application of said second signal to said patient's body.

70. The apparatus of claim 69, further comprising means for displaying information.

* * * * *